United States Patent [19]

Di Trapani et al.

[11] Patent Number: 4,585,586

[45] Date of Patent: Apr. 29, 1986

[54] PARTIALLY RETRO-INVERTED DECAPEPTIDE AS A SPECIFIC RENIN INHIBITOR WITH HIGH RESISTANCE TO ENZYMATIC HYDROLYSIS

[75] Inventors: Romano Di Trapani; Massimo Pinori; Antonio S. Verdini, all of Monterotondo, Italy

[73] Assignee: Ente Nazionale Idrocarburi, Rome, Italy

[21] Appl. No.: 612,799

[22] Filed: May 22, 1984

[30] Foreign Application Priority Data

May 25, 1983 [IT] Italy ................................. 21282 A/83

[51] Int. Cl.[4] .......................................... C07C 103/52
[52] U.S. Cl. ............................................. 260/112.5 R
[58] Field of Search ................................. 260/112.5 R

[56] References Cited

U.S. PATENT DOCUMENTS 4,439,360 3/1984 Verdini et al. ............... 260/112.5 R

OTHER PUBLICATIONS

Szelke et al., *Supp. II, Hypertension*, vol. 4, No. 3, 59–69, (1982).

*Primary Examiner*—Delbert R. Phillips
*Assistant Examiner*—F. T. Moezie

*Attorney, Agent, or Firm*—Hedman, Gibson, Costigan & Hoare

[57] ABSTRACT

Synthesis of an analogue of the (5–14) decapeptide of equine angiotensinogen partially retro-inverted at the Phe-Phe bond, of formula:

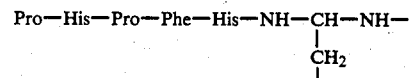
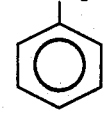
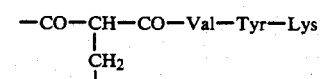
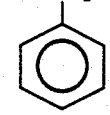

The retro-inverso analogue inhibits renin with high resistance to enzymatic degradation, and can be used in the treatment of renin-dependent hypertension.

4 Claims, No Drawings

PARTIALLY RETRO-INVERTED DECAPEPTIDE AS A SPECIFIC RENIN INHIBITOR WITH HIGH RESISTANCE TO ENZYMATIC HYDROLYSIS this invention relates to an analogue of the (5-14) decapeptide of equine angiotensinogen which is partly retro-inverted at the Phe-Phe bond, is a specific renin inhibitor with high resistance to enzymatic hydrolysis, and has prolonged in vivo activity.

Renin is one of the enzymatic components of the renin-angiotensin system illustrated hereinafter, the products of which perform physiologically important roles in maintaining cardiovascular homeostasis and contribute Ito the increase in arterial pressure in various hypertensive states [S. Oparil and E. Haber, New England J. Med. 291, 389 (1974); W. S. Peart, New England J. Med. 292, 302 (1975); E. Haber et al., Clin. Sci. Mol. Med. 48, 49 s (1975); J. O. Davis, Clin. Sci. Mol. Med. 48, 30 (1975)].

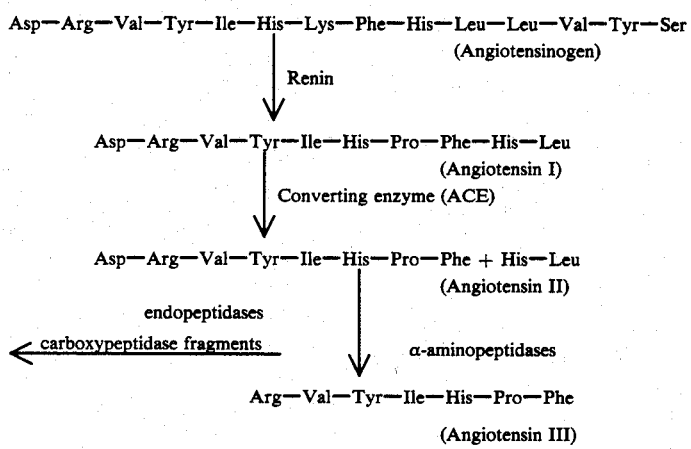

Renin, produced and released by the kidney juxtaglomerular cells, reacts with the renin substrate (angiotensinogen) to produce angiotensin I, an inactive decapeptide, which itself is converted, mainly in the lung, to angiotensin II by the angiotensin converting enzyme (ACE). Antiotensin II is the most powerful endogenous substance of pressor action which has been known up to the present time, and participates in regulating the release of renin by means of a direct feedback mechanism.

The renin-angiotensin system also constitutes one of the main mmechanisms for controlling the secretion of aldosterone from the suprarenal cortex, and the release of aldosterone is known to determine retention of Na+, fluids and caliuresis. Compounds which are inhibitors of the renin-angiotensin system are currently used for treating hypertension. Said compounds have the drawback of producing side effects such as the onset of compensatory hyperreninemia.

Moreover, recent experimental studies have shown that renin is present and is synthesised in the vascular smooth musculature, and could therefore play a not insignificant role in maintaining blood pressure. It has therefore been considered opportune to research the field of specific renin inhibitors for treating hypertension. Said inhibitors pertain to the following three classes:

(1) pepstatin and analogues
(2) lipids and phospholipids
(3) renin substrate analogues However, pepstatin and analogues are very effective in reducing blood pressure only in animal hypertension models ($I_{50}$ 0.1 $\mu$M), are ineffective in normotensive rats, and also have poor inhibition specificity, in that they act not only on renin but also on other acid proteases such as pepsin, isorenins and cathepsin D. The antihypertensive activity of lipids and phospholipids, which has been repeatedly observed in vitro, has recently been questioned, as has their importance as physiological regulators of the renin-angiotensin system. [M. J. Antonaccio and D. W. Cushman, Federation Proc. 40, 2275 (1981)].

Much interest has however been aroused by the compounds of the third class, the synthetic peptide inhibitors, in the form of structural analogues of renin substrate fragments incorporating the bonds $Leu^{10}$-$Leu^1$-land $Leu^{10}$-$Val^{11}$ hydrolysed by renin. Said compounds are very potent inhibitors ($I_{50}$ from 5.9 $\mu$M to 10 $\mu$M) and are highly specific. [J. Burton et al., Proc. Acad. Sci. U.S.A., 77, 5476 (1980); M. Szelke et al., European Patent Application No. 0-045-665, (1982); M. Szelke et al., Nature, 299, 555 (1982)]. Of these, the octapeptide His-Pro-Phe-His-Leu-Val-Ile-His and the decapeptide Pro-His-Pro-Phe-His-Leu-Val-Ile-His-Lys of the N-terminal sequence of human angiotensinogen, in which the hydrolysable Leu-Val bond has been reduced to —$CH_2$—NH— in order to block hydrolysis by the renin, and the decapeptide Pro-His-Pro-Phe-His-Phe-Phe-Val-Tyr-Lys of the N-terminal sequence of equine angiotensinogen have been synthesised.

However, this latter decapeptide, which is a specific inhibitor of human renin in vitro and an effective in vivo antihypertensive, has a very short action duration (about 4 minutes) and this represents a limitation to its clinical application (J. Burton, U.S. Pat. No. 4,269,827).

An inhibitor peptide which is specific for renin and having a high resistance to enzymatichydrolysis and a prolonged time of action has now been discovered, and forms the subject matter of the present invention.

The use of renin inhibitors with prolonged action has the following consequences:

(1) it prevents the onset of compensatory hyperreninemia, which generally occurs during the use of current inhibitors of the renin-angiotensin system;
(2) it enables long-duration in vivo experiments to be carried out in studies on chronic renin-dependent hypertensive forms.

One of the main causes of the limited in vivo stability of the decapeptide and thus of its non-persistent antihypertensive action seems to be connected with the ease with which it is hydrolysed by the action of the renin itself and of the other peptidases of the blood plasma.

Consequently, in order to obtain adequate protection of the peptide substances against the proteolytic action of proteases, it has been found very advantageous to use the method of retro-inverting those peptide bonds which are most susceptible to enzymatic hydrolysis.

Inverting the direction of the peptide bonds

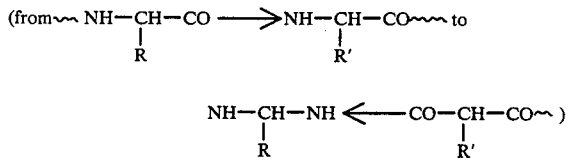

as described in the U.S. application Ser. Nos. 448,831,448,832, EP. Appln. Publ. No. 0097994, It. Appln. Nos. 20926A/82,23417A/82 produces analogues known generically as "retro-inverso peptides" which are structural isomers of the reference peptides and as such preserve their biological activity while being generally more resistant to enzymatic hydrolysis.

According to the present invention, we have inverted the Phe-Phe bond of the decapeptide Pro-His-Pro-Phe-His-Phe-Phe-Val-Tyr-Lys, which is situated at the hydrolytic action site of renin, to obtain an analogue capable of inhibiting the enzyme with an in vivo activity more prolonged than that of the inhibitor with all its peptide bonds normal.

The inversion of a single peptide bond in the sequence involves transforming the two engaged amino acid residues in order to form the inverted bond, and in particular transforming the amino acid residue closest to the amino end of the reference peptide into a gem-diamino residue, and transforming the amino acid residue closest to the carboxyl end into a malonyl or 2-substituted malonyl residue. [Goodman M. et al., Acc. Chem. Res. 12 (1979)].

Incorporating the malonyl or 2-substituted malonyl residues into the peptide skeleton does not present special problems, whereas incorporating gem-diamino residues generally requires delicate synthesis manipulations, which have been accomplished as described in the aforesaid preceding cited patent applications by the use of 1,1-bis(trifluoroacetoxy)iodobenzene (TIB).

This reagent had been previously used for the direct conversion of primary simple structure amides into amines without the need for isolating or capturing the intermediate isocyanate [Radhakrishna A. S. et al., J. Org. Chem. 44, 1746 (1979)].

The retro-inverso peptide of the present patent application is represented by the formula:

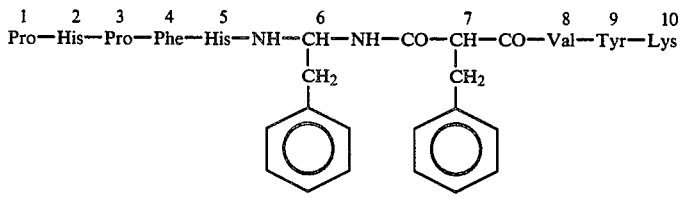

where the amino acids are all of L configuration, the asymmetric carbon of the gem-diamino residue has the same configuration as the L-phenylalanine, and the asymmetric carbon of the malonyl residue can possess R or S configuration, or a mixture of the two configurations.

The aforesaid peptide can be obtained by:

(a) Synthesis of the two fragments 1-6 and 7-10.
(b) Transformation of the terminal carboxyamide group of the 1-6 fragment into an amino group by treatment with TIB in accordance with a method described in patent application U.S. Ser. No. 448,831.
(c) Condensing said fragments, partially protected by temporary protector groups chosen from those known in the peptide synthesis art and compatible with the synthesis strategies adopted in the preparation of said fragments.
(d) Unblocking said protector groups in a single stage by treatment with trifluoroacetic acid (TFA) and final chromatographic purification of the mixture of the two diastereoisomers, which can then be separated by high pressure preparative chromatography on carboxymethyl cellulose supports.

The condensation of the two fragments can be conducted by one of the methods known in peptide synthesis, and preferably by the method using N,N'-dicyclohexylcarbodiimide and 1-hydroxybenzotriazole as the mixture condensing agent.

The partially protected peptide fragment:

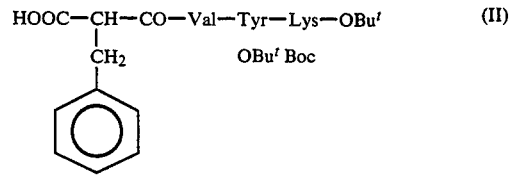

was obtained in the homogenous phase by the following series of reactions, using a synthesis strategy comprising successive stages starting from:

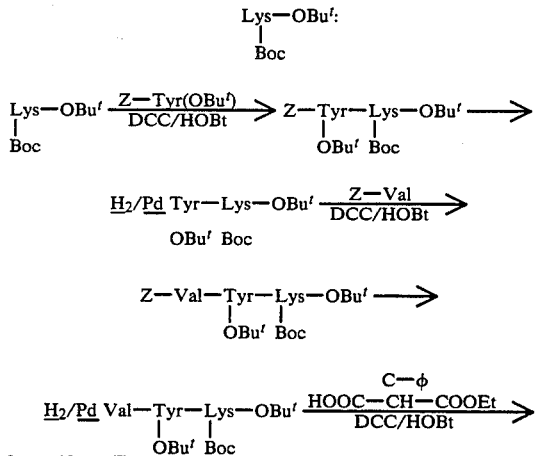

-continued

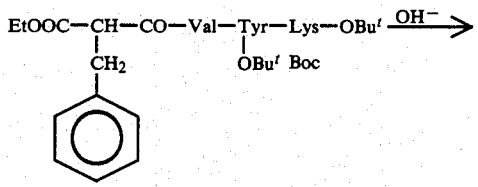

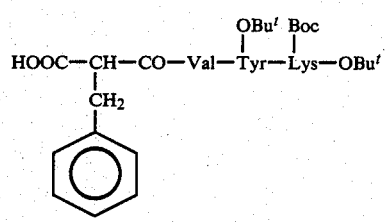

The partially protected fragment:

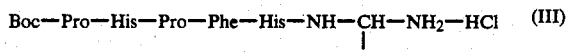

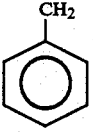

was obtained by treating the peptide amide Boc-Pro-His-Pro-Phe-His-Phe-NH$_2$ (IV) with the reagent 1,1-bis(trifluoroacetoxy)iodobenzene, with subsequent exchange of the resultant trifluoroacetate with HCl.

The amide (IV) can itself be conveniently prepared by the usual methods of peptide synthesisin the solid phase, which as known to experts of the art consists of constructing the sequence by adding the individual amino acids in successive stages on polymer matrices which are insoluble but swellable in the reaction medium, and to which the peptide remains bound until termination of the synthesis, and from which it is released by treatment with a suitable reagent.

The polymer used in the synthesis according to the present patent application is constituted by beads of polyamide resin which has been suitably functionalised with substituted benzyl alcohol residues [R. Arshady et al., J. Chem. Soc., Perkin I 529 (1981)].

The first phenylalanine ammino acid residue, activated separately under suitable conditions, is bound to these residues by an ester linkage, as a symmetrical anhydride. The substituted benzyl alcohol residue connecting the peptide to the resin insoluble during the synthesiswas chosen in such a manner that the peptide could be detached from the resin directly in the amide form (IV) on termination of the synthesis by treatment with NH$_3$.

The tests to determine the renin inhibition by the peptide analogue according to the present invention can be conducted as described by Millar and collaborators [J. A. Millar et al., Clinica Chim. Acta 101, 5 (1980)]. In this test, the rate of generation of angiotensin I from human angiotensinogen by human plasmatic renin at pH 7.0 is measured by radioimmunoassay of antibody binding. The rate of generation of angiotensin I in the presence of the inhibitor can be expressed generally as a percentage of that measured in the absence of inhibitor.

The increased stability of the retro-inverso peptide to peptidases compared with the peptide without inverted bonds under the inhibition test conditions can be evaluated either in the absence or in the presence of peptidase inhibitors such as EDTA, o-phenanthroline, benzamidine hydrochloride and trasylol, and either with or without preincubation in the human plasma.

The retro-inverso peptide of the present invention is a potent selective renin inhibitor with a duration of action which is more prolonged than that of the peptide with all its peptide bonds normal.

EXAMPLE

Preparation of the Peptide (1) Preparation of the (1-6) fragment (a) Boc-Pro-His-Pro-Phe-His-Phe-NH$_2$ The synthesis was conducted in the solid phase by the method described by Sheppard and collaborators [E. Atherton et al., J. Chem. Soc. Perkin I, 538 (1981)], with certain modifications. 1 g of polymer support constituted by beads of polydimethylamideco-acryloylsarcosine methyl ester cross-linked with N,N'-ethylenebisacrylamide, was activated by treatment with 1,2-diaminoethane.

The activated resin was reacted with 1.8 mmoles of (Fmoc Nle)$_2$O and then, after removing the Fmoc by treatment with 20% piperidine in dimethylformamide (DMF), it was acylated with 1.8 mmoles of 2,4,5-trichlorophenol-p-hydroxymethylbenzoate.

The resin modified in this manner contained 0.525 mmoles/g of norleucine.

The ester linkage with the first amino acid was formed by treating the modified resin for 30 minutes with 1.8 mmoles of (Fmoc Phe)$_2$O dissolved in 16 ml of DMF in the presence of 1.8 mmoles of N-methylmorpholine and 0.18 mmoles of 4-dimethylaminopyridine. This reaction, and the subsequent ones until the synthesis of the entire hexapeptide was complete, was conducted in the reaction vessel of an automatic Beckman ® synthesizer, model 990B.

The subsequent amino acids were introduced sequentially into the polymer in the order described in Table 1, following one of the procedures of Table 2.

The acylations were conducted by reacting the resin for 60 min with 1.8 mmoles of symmetrical anhydride of the protected amino acid.

The anhydrides were preformed at the moment of acylation: 3.6 mmoles of protected amino acid were reacted with 1.8 mmoles of N,N'-dicyclohexylcarbodiimide in CH$_2$Cl$_2$ at ambient temperature for 10 min, the dicyclohexylurea formed was filtered off, the CH$_2$Cl$_2$ was evaporated under vacuum, and the symmetrical anhydride was redissolved in 16 ml of DMF.

For each acylation, completion of the formation of the amide bond was verified by reacting a sample of resin with ninhydrin in accordance with the method of Kaiser [E. Kaiser, Anal. Biochem. 34, 595 (1970)]. Amino acid analysis was carried out on samples hydrolysed for 18 hours at 110° C. with HCl to constant boiling point, in the presence of phenol, in closed vials under vacuum. After adding the last amino acid, the resin was suspended in methanol saturated with ammonia, and left in a properly closed vessel at ambient temperature for 2 hours.

After evaporating the ammonia, the peptide was separated by filtration and washing the resin with 2N AcOH. 500 μmoles of crude peptide were obtained by evaporating the solution.

The peptide was dissolved in 100 ml of water, the pH adjusted to 4.5 with acetic acid, and the solution chromatographed on Sephadex® SP-C25 (1.6×25 cm) with a linear ammonium acetate gradient (from 0.05 to 0.5N in 7 hours) with a flow rate of 60 ml/h.

The fractions of the main peak were lyophilised twice to obtain 400 μmoles of peptide.

Amino acid analysis: 2Pro, 2.07; 2His, 1.94; 2Phe, 2.00.

The peptide was analysed by high pressure liquid chromatography on a 82 Bondapak® C-18 (10μ) column eluted with an aqueous phase containing 0.1% of TFA and modified with $CH_3CN$ (33.5% by volume). The isolated peptide was 90% pure. The impurities were identified as Boc-peptide methylester.

(b)

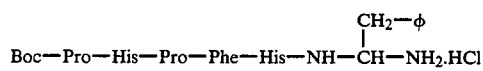

Boc—Pro—His—Pro—Phe—His—NH—CH—NH$_2$.HCl

The peptide obtained in (a) was dissolved in 60 ml of $CH_3CN/H_2O$ (3:2 v/v). 300 mg (800 μmoles) of bis-1,1-bis (trifluoroacetoxy) iodobenzene were added to the solution, and the mixture was left under agitation at ambient temperature for 3 hours.

After evaporating the $CH_3CN$, the solution was diluted with water, filtered and chromatographed on Sephadex® SP-C25 (1.6×25 cm) under the same conditions as described in a).

The fractions of the main peak were diluted with water containing 1 meq of HCl and lyophilised twice.

330 μmoles of peptide were obtained.

Amino acid analysis: 2Pro, 2.0; 2His, 1.98; 1Phe, 1.05.

The peptide was analysed by high pressure liquid chromatography under the same conditions as described in (a). The chromatogram showed a single peak.

(2) Preparation of the (7-10) Fragment (a) Z-Tyr(OBu$^t$)-Lys(Boc)OBu$^t$. A solution containing 1.6 g (4.3 mmoles) of N-benzyloxycarbonyl-L-tyrosine O-tert.butylether in 20 ml of $CH_2Cl_2$ was cooled to 0° C. and 0.58 g (4.3 mmoles) of 1-hydroxybenzotriazole and 0.89 g (4.3 mmoles) of N,N'-dicyclohexylcarbodiimide were added.

After 30 min the mixture was filtered, and the filtrate added to a solution containing 1.38 g (4.1 mmoles) of tert.butyl N-tert.butyloxycarbonyl-L-lysinate in 10 ml of $CH_2Cl_2$.

After 3 hours the solvent was evaporated and the residue taken up in ethyl acetate, the solution was filtered and washed with 5% $NaHCO_3$, 20% citric acid and water in that order. The organic phase was dried with anhydrous $MgSO_4$ and evaporated to obtain an oil, which was crystallised with ethyl ether. 1.7 g (60%) of a white product of M.P. 114–115° C. were obtained. The product showed a single spot in thin layer liquid chromatography in at least three eluent systems. The proton n.m.r. spectrum confirmed the molecular structure.

(b) Z-Val-Tyr(OBu$^t$)Lys(Boc)OBu$^t$. 1.35 g (2.6 mmoles) of Tyr(OBu$^t$)-Lys(Boc)OBu$^t$ formed by catalytic hydrogenation of the product obtained from the procedure described in (a) were reacted with 0.67 g (2.66 mmoles) of N-carbobenzoxy-L-valine under the conditions described in (a).

After crystallising from ethyl acetate/n-hexane, 1,4 g (70%) of pure product were obtained. The purity of the compound was ascertained by examining the proton n.m.r. spectrum and by thin layer liquid chromatography in various eluent systems.

(c)

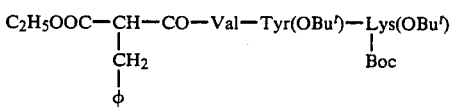

$C_2H_5OOC$—CH—CO—Val—Tyr(OBu$^t$)—Lys(OBu$^t$)
         |                              |
        $CH_2$                          Boc
         |
         φ

1.0 g (1.6 mmoles) of Val-Tyr(OBu$^t$)-Lys(Boc)OBu$^t$, formed by catalytic hydrogenation of the product obtained from the procedure described in (b), was reacted under the conditions described in (a) with 0.4 g (1.8 mmoles) of 2-benzylmalonic monoethylester obtained by hemisaponifying the corresponding diethylester with KOH. After crystallisation from ethyl acetate/n-hexane, 1.03 g (78%) of product with a M.P. of 145°-148° C. were obtained. Both the proton n.m.r. spectrum and thin layer liquid chromatography demonstrated the purity of the compound.

(d)

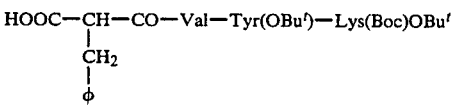

HOOC—CH—CO—Val—Tyr(OBu$^t$)—Lys(Boc)OBu$^t$
      |
     $CH_2$
      |
      φ

1.03 g (1.25 mmoles) of the ethyl ester obtained by the procedure described in (c) were dissolved in 30 ml of absolute ethyl alcohol, and 3 ml of 2N KOH were added drop by drop. After one hour, 6 ml of 1N HCl were added, and after evaporating the solvent and dissolving in water, the pH was adjusted to 2 with HCl, and the solution extracted repeatedly with ethyl acetate. The organic phase was dried with anhydrous $MgSO_4$, and the solvent was evaporated under vacuum. An oil was obtained which was crystallised from ethyl acetate/n-hexane.

880 mg (88%) of a white solid product with a M.P. of 110°-113° C. were obtained.

Thin layer liquid chromatography in various eluent media and the proton n.m.r. spectrum demonstrated the purity of the compound.

Elementary analysis: calculated: C 64.8%; N 7.03%; H 8.04%, found: C 64.4%; N 7.02%; H 7.9%.

(3) Condensation of the (1-6) and (7-10) Fragments and Total Deprotection 200 mg (250 μmoles) of the partially protected (7-10) fragment were dissolved in 2 ml of N,N-dimethylformamide (DMF). 34 mg (250 μmoles) of 1-hydroxybenzotriazole and 52 mg (250 μmoles) of N,N'-dicyclohexylcarbodiimide were added to the solution cooled to 0° C. After one hour at 0° C., the mixture was filtered and the filtrate added to a solution containing 50 μmoles of the (1-6) fragment dissolved in 1 ml of DMF. The pH of the solution was adjusted to 9.0 with triethylamine. After 24 hours at ambient temperature the mixture was evaporated under high vacuum, and the residue was treated twice with a saturated $NaHCO_3$ solution. The white solid obtained was then washed with water until neutral pH.

The solid residue, dissolved in 3 ml of 95% aqueous TFA (v/v) was kept at ambient temperature for 30 minutes. After evaporating the solvent under high vacuum, the residue was dissolved in water and lyophilised several times. The pH of a solution of the lyophilised product in 170 ml of water was adjusted to 7.0 with 0.1M NH₄OH, and the solution was then chromatographed on carboxymethylcellulose ® CM-52 (0.9×9 cm) eluting with a linear gradient of ammonium acetate (from 0.01 to 0.2N in 12 hours) with a flow rate of 60 ml/h.

The fractions eluted between 180 ml and 230 ml were pooled and lyophilised several times.

35 μmoles (70%) of peptide were obtained.

Amino acid analysis: 2Pro, 2.05; 2His, 2.09; 1Phe, 0.97; 1Val, 0.90; 1Tyr, 0.95; 1Lys, 1.00.

The peptide was analysed by high pressure liquid chromatography with a Lichrosorb ® RP-18 (5μ) column, eluting with an aqueous phase containing 0.1% of TFA and modified with CH₃CN (38% by volume). Only two peaks were observed corresponding to the two diastereoisomers due to the R, S configuration of the malonyl residue. The peptide showed a single spot (observable by ninhydrin and with Pauly reagent) under high voltage electrophoresis on a thin layer of microcrystalline cellulose (buffers: formic acid/acetic acid pH 2.1; sodium acetate/acetic acid pH 3.5).

TABLE 1
ORDER OF ADDING THE AMINO ACIDS USED IN THE SYNTHESIS, AND THE PROCEDURE USED

| | AMINO ACID DERIVATIVE | PROCEDURE |
|---|---|---|
| 1 | Fmoc—Phe | A |
| 2 | N,N$^{im}$—di-Boc—His | A |
| 3 | Fmoc—Phe | B |
| 4 | Fmoc—Pro | A |
| 5 | N,N$^{im}$—di-Boc—His | A |
| 6 | Boc—Pro | B |

TABLE 2
PROCEDURES FOR SOLID PHASE SYNTHESIS ON POLYAMIDE MATRICES

| A | | B | |
|---|---|---|---|
| 1 | 5 washes with DMF | 1 | 5 washes with t.amyl alcohol |
| 2 | 2 treatments with 20% piperidine in 20% in DMF | 2 | 5 washes with acetic acid |
| 3 | 10 washes with DMF | 3 | 2 treatments with 1N HCl in acetic acid |
| 4 | acylation | 4 | 5 washes with acetic acid |
| 5 | 5 washes with DMF | 5 | 5 wahses with t.amyl alcohol |
| | | 6 | 10 washes with DMF |
| | | 7 | 3 treatments with 10% diisopropylethylamine in DMF |
| | | 8 | 5 washes with DMF |
| | | 9 | acylation |
| | | 10 | 5 washes with DMF |

(A) PROCEDURE USED WHEN THE AMINO ACID OF THE GROWING END IS PROTECTED BY FMOC
(B) PROCEDURE USED WHEN THE AMINO ACID OF THE GROWING END IS PROTECTED BY BOC

We claim:

1. A peptide retro-inverted at the Phe-Phe bond, as a specific renin inhibitor and possessing high resistance to enzymatic hydrolysis and prolonged in vivo inhibition activity, of the following formula:

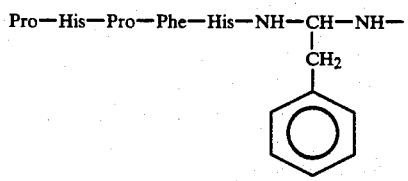
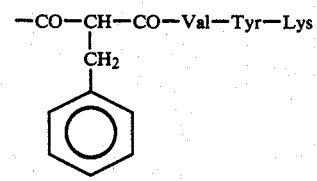

2. A peptide as claimed in claim 1, wherein the gem-diamino residue

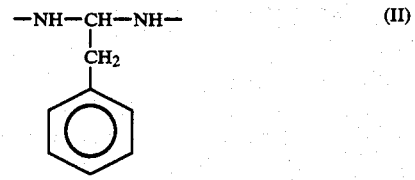

possesses S configuration, and the malonyl residue

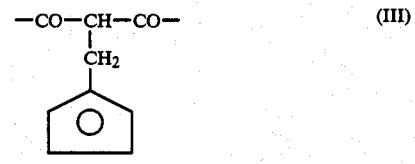

is R or S enantiomers.

3. A peptide as claimed in claim 1, wherein the gem-diamino residue (II) possesses S configuration and the malonyl residue (III) possesses S configuration.

4. A peptide as claimed in claim 1, wherein the gem-diamino residue (II) possesses S configuration and the malonyl residue (III) possesses R configuration.

* * * * *